US008781065B2

(12) United States Patent
Taylor et al.

(10) Patent No.: US 8,781,065 B2
(45) Date of Patent: Jul. 15, 2014

(54) APPARATUS AND A METHOD OF DETERMINING THE PROPORTIONS OF DIFFERENT POWDERS IN A POWDER

(75) Inventors: Jonathan M. Taylor, Derby (GB); Michael L. Blackmore, Sheffield (GB)

(73) Assignee: Rolls-Royce PLC, London (GB)

( * ) Notice: Subject to any disclaimer, the term of this patent is extended or adjusted under 35 U.S.C. 154(b) by 348 days.

(21) Appl. No.: 13/429,765

(22) Filed: Mar. 26, 2012

(65) Prior Publication Data

US 2012/0257712 A1    Oct. 11, 2012

(30) Foreign Application Priority Data

Apr. 8, 2011 (GB) .................................. 1105926.8

(51) Int. Cl.
  *G01N 23/083* (2006.01)
  *G01N 23/04* (2006.01)
  *G01N 15/08* (2006.01)
(52) U.S. Cl.
  CPC ............ *G01N 15/088* (2013.01); *G01N 23/046* (2013.01); *G01N 2015/0846* (2013.01); *G01N 2015/0833* (2013.01)
  USPC .......................................................... 378/51
(58) Field of Classification Search
  CPC .... G01N 23/04; G01N 23/046; G01N 15/088
  USPC ........... 378/4–20, 45, 51, 53, 57, 83, 88, 901; 382/128–131
  See application file for complete search history.

(56) References Cited

U.S. PATENT DOCUMENTS 4,982,086 A * 1/1991 Withjack ...................... 250/255
5,428,655 A    6/1995 Moriya et al.

OTHER PUBLICATIONS

Clemex Intelligent Microscopy, *Clemex Technologies Inc.*, pp. 1-12, 2007.
Brewin et al., *Modelling of Powder Die Compaction*, pp. 140-146, Section 9.6, 2008.
Search Report issued in British Application No. 1105926.8 dated Jul. 6, 2011.

* cited by examiner

*Primary Examiner* — Courtney Thomas
(74) *Attorney, Agent, or Firm* — Oliff PLC

(57) ABSTRACT

A method of determining the proportions of different powders in a powder comprises obtaining a sample of a powder, adding and mixing the sample into a molten material and freezing the mixture of powder and molten material to form a block. Computed tomography is performed on the block to produce a three-dimensional image of the block, the three-dimensional image of the block comprises a first shade, a second and a third shade corresponding to the material, a first powder particle and a sec and powder particle. The three-dimensional image of the block is analyzed to count the number of regions exhibiting the second shade and the third shade corresponding to the number of first powder particles and second powder particles respectively. The fraction of second particles in the powder is determined by dividing the number of second powder particles by the sum of the number of first powder particles and the number of second powder particles.

24 Claims, 1 Drawing Sheet

APPARATUS AND A METHOD OF DETERMINING THE PROPORTIONS OF DIFFERENT POWDERS IN A POWDER

The present invention relates to an apparatus and a method of determining the proportions of different powders in a powder and more particularly to a method of determining the proportion of porosity in a powder, e.g. the proportion of powder particles containing pores in a powder.

Metal powder may be used to manufacture metal components for gas turbine engines and other industries by hot isostatic pressing the metal powder in a sealed shaped metal canister. Metal powder may be hot isostatically pressed to manufacture a billet which is subsequently forged. Metal powder may be hot isostatically pressed to manufacture net shape, or near net shape, components. Metal powder may be used in the manufacture and/or repair, of metal components for gas turbine engines, e.g. for the repair of blisks, integrally bladed disks.

It is important to know the proportion of powder particles containing pores and also the size, or diameter, of the pores within the powder particles.

The size of the pores within the powder particles and the proportion of powder particles containing a pore directly affects the working life of a component repaired with a metal powder, e.g. the smaller the proportion of powder particles containing a pore the greater the working life and/or the smaller the diameter of the pores within the powder particles the greater the working life.

The size of the pores within the powder particles and the proportion of powder particles containing a pore affect the amount of shrinkage during hot isostatic pressing of metal powder and this must be taken into account during the manufacture of net shape, or near net shape, components.

A book "Modelling of Powder Die Compaction" by Peter Brewin, Olivier Coube, Pierre Doremus and James H Tweed, ISBN: 978-1-84628-098-6, published 2008 discloses in Section 9.6.3 an experiment in which a rectangular Perspex die was filled with Distaloy AE powder. The Distaloy AE powder was then subjected to rotational computed tomography to generate a three-dimensional image of the powder particles to determine if any settling of the powder particles prior to compaction had occurred.

A Clemex PSA microscope may be used to view particles mounted in a resin and image processing may be used to measure the size and shape of the particles.

However, the prior art mentioned above only has the potential for a low throughput determination of porosity of a powder, using a non-scalable system. The prior art relies on adequate mixing and non-separation of a very powder sample, leading to unreliability in the determination of the porosity of the powder.

Accordingly the present invention seeks to provide an improved method of determining the proportions of different powders in a powder.

Accordingly the present invention provides a method of determining the proportions of different powders in a powder comprising the steps of:

a) obtaining a sample of a powder, the powder comprising powder particles,
b) preparing a predetermined volume of molten material,
c) adding the sample of the powder to the molten material,
d) mixing the sample of the powder into the molten material,
e) solidifying the mixture of powder and molten material to form a block, the block consisting of the material containing the powder particles,
f) carrying out computed tomography on the block to produce a three-dimensional image of the block, the three-dimensional image of the block comprising a first shade, or colour, corresponding to the material, a second shade, or colour, corresponding to a first powder particle and a third shade, or colour, corresponding to a second powder particle,
g) analysing the three-dimensional image of the block to count the number of regions exhibiting the second shade, or colour, and hence count the corresponding number of first powder particles in the block, analysing the three-dimensional image of the block to count the number of regions exhibiting the third shade, or colour, and hence count the corresponding number of second powder particles, and
h) determining the amount of second particles in the powder by determining the fraction of second powder particles by dividing the number of second powder particles counted in step g) by the sum of the number of first powder particles counted in step g) and the number of second powder particles counted in step g).

Step a) may comprise obtaining a sample of a metal powder, an alloy powder or a ceramic powder.

Step b) may comprise preparing a predetermined volume of a low melting point eutectic alloy.

The low melting point eutectic alloy may consist of a bismuth-tin eutectic alloy.

Step b) may comprise preparing a predetermined volume of a polymer/plastic or water.

The first and second powder particles may consist of different materials.

The first powder particles may be pore free and the second powder particles have pores and the first and second powder particles consist of the same material.

The method may further comprise measuring the diameter of each pore in a powder particle. The method may further comprise calculating the mean diameter of the pores, the maximum diameter of the pores, the minimum diameter of the pores or the variance in the diameter of the pores.

Step f) may comprise X-ray computed tomography.

Step f) may comprise carrying out computed tomography on the block to produce a three-dimensional image of the block, the three-dimensional image of the block comprising a first shade, or colour, corresponding to the material, a second shade, or colour, corresponding to a first powder particle, a third shade, or colour, corresponding to a second powder particle and a fourth shade, or colour, corresponding to a third powder particle, g) analysing the three-dimensional image of the block to count the number of regions exhibiting the second shade, or colour, and hence count the corresponding number of first powder particles in the block, analysing the three-dimensional image of the block to count the number of regions exhibiting the third shade, or colour, and hence count the corresponding number of second powder particles, analysing the three-dimensional image of the block to count the number of regions exhibiting the fourth shade, or colour, and hence count the corresponding number of third powder particles, and h) determining the amount of second particles in the powder by determining the fraction of second powder particles by dividing the number of second powder particles counted in step g) by the sum of the number of first powder particles counted in step g), the number of second powder particles counted in step g) and the number of third powder particles counted in step g).

Step e) may comprise freezing the molten material, e.g. the molten low melting point eutectic alloy or the water.

The present invention also provides a method of determining the proportion of porosity in a powder comprising the steps of:

a) obtaining a sample of a powder, the powder comprising powder particles, b) preparing a predetermined volume of molten material, c) adding the sample of the powder to the molten material, d) mixing the sample of the powder into the molten material, e) solidifying the mixture of powder and molten material to form a block, the block consisting of the material containing the powder particles, f) carrying out computed tomography on the block to produce a three-dimensional image of the block, the three-dimensional image of the block comprising a first shade, or colour, corresponding to the material, a second shade, or colour, corresponding to a powder particle and a third shade, or colour, corresponding to a pore in a powder particle, g) analysing the three-dimensional image of the block to count the number of regions exhibiting the second shade, or colour, and hence count the corresponding number of powder particles in the block, analysing the three-dimensional image of the block to count the number of regions exhibiting the third shade, or colour, and hence count the corresponding number of powder particles containing a pore, and h) determining the amount of porosity in the powder by determining the fraction of powder particles containing pores by dividing the number of powder particles containing a pore counted in step g) by the number of powder particles counted in step g).

The present invention also provides an apparatus for determining the proportions of different powders in a powder comprising a computed tomography device operable to produce a three-dimensional image of a block, the block consisting of a material containing powder particles, the three-dimensional image of the block comprising a first shade, or colour, corresponding to the material, a second shade, or colour, corresponding to a first powder particle and a third shade, or colour, corresponding to a second powder particle, a processor arranged to analyse the three-dimensional image of the block to count the number of regions exhibiting the second shade, or colour, and hence count the corresponding number of first powder particles in the block, a processor arranged to analyse the three-dimensional image of the block to count the number of regions exhibiting the third shade, or colour, and hence count the corresponding number of second powder particles, and a processor arranged to determine the amount of second particles in the powder by determining the fraction of second powder particles by dividing the number of second powder particles counted by the sum of the number of first powder particles counted and the number of second powder particles counted.

The second powder particles may comprise pores, the apparatus further comprising a calculator to calculate the mean diameter of the pores, the maximum diameter of the pores, the minimum diameter of the pores or the variance in the diameter of the pores.

The computed tomography device may comprise an X-ray computed tomography device.

The present invention will be more fully described by way of example with reference to the accompanying drawings, in which.

Figure 1:
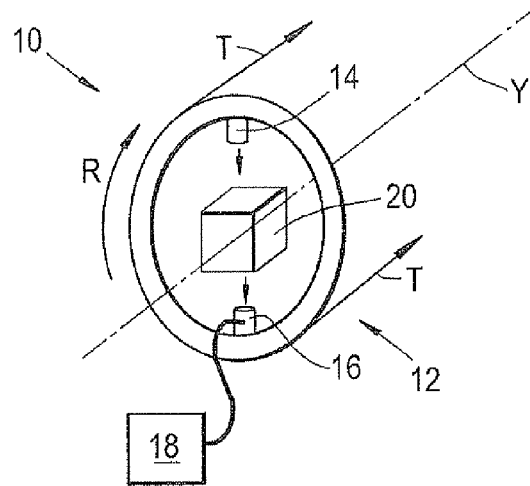
FIG. 1 is a schematic perspective illustration of an apparatus for use in a method of determining the proportions of different powders in a powder according to the present invention.

FIG. 1 shows an apparatus 10 for use in a method of determining the proportions of different powders in a powder. The apparatus 10 comprises an X-ray computed tomography device 12 which comprises an X-ray source 14 and an X-ray detector 16. The X-ray source 14 and X-ray detector 16 are arranged to rotate, as shown by arrow R, as a unit around an axis Y with the X-ray source 14 and the X-ray detector 16 arranged diametrically opposite each other. The X-ray source 14 and the X-ray detector 16 are also arranged to translate, as shown by arrow T, together as a unit in the direction of the axis Y. The X-ray detector 16 is connected to a processor 18, e.g. a computer, and the X-ray detector 16 is arranged to send signals containing information concerning the intensity of the X-rays received by the X-ray detector 16 to the processor 18. FIG. 1 also shows a block of material 20 arranged to be inspected by the X-ray computed tomography device 12.

Figure 2:
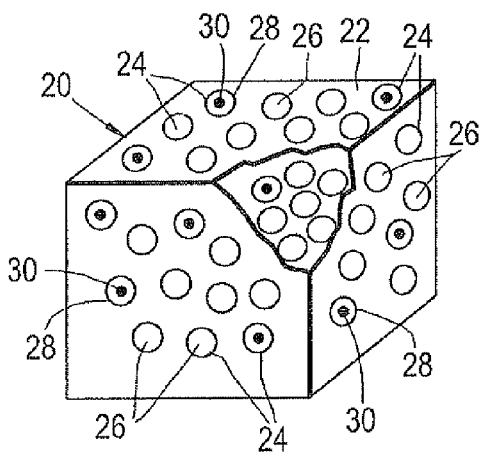
FIG. 2 is an enlarged cut away perspective view of a block of material containing different powders used in a method of determining the proportions of different powders in a powder according to the present invention.

FIG. 2 shows a block of material 20 to be inspected by the X-ray computed tomography device 12. The block of material 20 consists of a matrix material 22 which contains a powder 24. The powder 24 comprises powder particles of different powders, for example first powder particles 26 and second powder particles 28. In this example the first powder particles 26 are solid powder particles and the second powder particles 28 are porous powder particles, e.g. the second powder particles 28 contain a pore 30. The first and second powder particles 26 and 28 consist of the same material, e.g. the same metal, or alloy, or ceramic etc.

Figure 3:
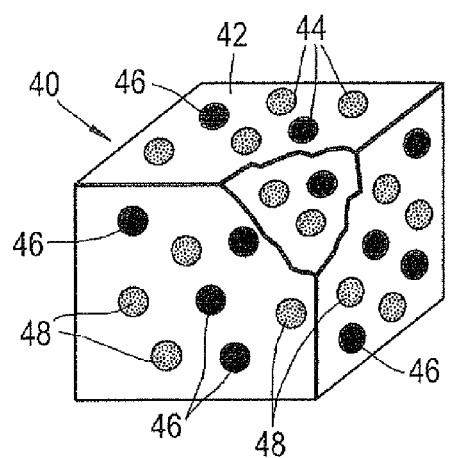
FIG. 3 is an enlarged cut away perspective view of a second block of material containing different powders used in a method of determining the proportions of different powders in a powder according to the present invention.

FIG. 3 shows another block of material 40 to be inspected by the X-ray computed tomography device 12. The block of material 40 consists of a matrix material 42 which contains a powder 44. The powder 44 comprises powder particles of different powders, for example first powder particles 46 and second powder particles 48. In this example the first powder particles 46 are solid powder particles and the second powder particles 48 are solid powder particles and the first and second powder particles 46 and 48 consist of different materials, e.g. different metals, or different alloys, or different ceramics, or a metal and a ceramic etc.

In a first method of determining the proportions of different powders in a powder 24 according to the present invention a sample of a powder 24 is obtained, the powder 24 comprising powder particles 26 and 28. A predetermined volume of a molten material 22 is prepared. In this example a predetermined volume of a low melting point eutectic alloy, e.g. low melting point bismuth-tin eutectic alloy, is prepared. The sample of powder 24 is then added to the molten material 22 and the powder 24 is mixed into the molten material 22. The mixture of powder 24 and molten material 22 is then frozen or solidified, in this example the low melting point eutectic alloy is cooled below its melting point so that it solidifies, to form a block 20 such that the block 20 consists of the material 22 containing the powder particles 24, or powder particles 24 distributed in a matrix material 22 as shown in FIG. 2.

Then the block 20 of FIG. 2 is placed in the X-ray computed tomography device 12 and X-ray computed tomography is performed on the block 20 to produce a three-dimensional image of the block 20. During the X-ray computed tomography X-rays are directed from the X-ray source 14 at a first axial position, is with respect to the axis Y, through the block 20 and X-rays are detected by the X-ray detector 16 at the opposite side of the block 20. The X-ray source 14 and X-ray detector 16 are rotated around the axis Y at the first axial position to view the block 20 from all angles around the axis Y at the first axial position. The X-ray source 14 and the X-ray detector 16 are then moved incrementally in the direction of the axis Y and the X-ray source 14 and X-ray detector 16 are rotated around the axis Y at each incremental axial position to view the block 20 from all angles around the axis Y at each incremental axial position. The X-ray detector 16 sends signals to the processor 18 concerning the intensity of the X-rays detected by the X-ray detector 16 for each angle at each axial position of the block 20.

The processor 18 produces a three-dimensional image of the block 20 and the three dimensional image of the block 20 comprises a first shade, or colour, corresponding to the material 22, a second shade, or colour, corresponding to the first powder particles 26 and a third shade, or colour, corresponding to the second powder particle 28, 30. The processor 18 analyses the three-dimensional image of the block 20 and counts the number of regions exhibiting the second shade, or colour, and hence counts the corresponding number of first powder particles 26 in the block 20. The processor 18 analyses the three-dimensional image of the block 20 and counts the number of regions exhibiting the third shade, or colour, and hence counts the corresponding number of second powder particles 28, 30. Although the first and second powder particles 26 and 28 consist of the same material the second powder particles 28 are different to the first powder particles 26 because the second powder particles 28 have pores 30 and the pores 30 affect the intensity of the X-rays received by the X-ray detector 16. The processor 18 then determines the amount of second powder particles 28, 30 in the powder 24 by determining the fraction of second powder particles 28, 30 by dividing the number of second powder particles 28, 30 counted by the sum of the number of first powder particles 26 counted and the number of second powder particles 28, 30 counted.

The processor 18 may measure the diameter of each pore 30 in a powder particle 28. The processor 18 may calculate the mean diameter of the pores 30, the maximum diameter of the pores 30, the minimum diameter of the pores 30 or the variance in the diameter of the pores 30.

The powder 24 may comprise a metal powder, an alloy powder, a ceramic powder, a mixture of a metal powder and an alloy powder, a mixture of a metal powder and a ceramic powder or a mixture of an alloy powder and a ceramic powder.

The molten material 22 may alternatively comprise a polymer/plastic or water and the molten material 22 is solidified after the sample of powder 24 has been added to the molten material 22.

It may be possible to use other types of computed tomography, in place of X-ray computed tomography.

In a second method of determining the proportions of different powders in a powder 44 according to the present invention a sample of a powder 44 is obtained, the powder 44 comprising powder particles 46 and 48. A predetermined volume of a molten material 42 is prepared. In this example a predetermined volume of a low melting point eutectic alloy, e.g. low melting point bismuth-tin eutectic alloy, is prepared. The sample of powder 44 is then added to the molten material 42 and the powder 44 is mixed into the molten material 42. The mixture of powder 44 and molten material 42 is then frozen, or solidified, e.g. cooled below its melting point so that it solidifies, to form a block 40 such that the block 40 consists of the material 42 containing the powder particles 44, or powder particles 44 distributed in a matrix material 42 as shown in FIG. 3.

Then the block 40 of FIG. 3 is placed in the X-ray computed tomography device 12 and X-ray computed tomography is performed on the block 40 to produce a three-dimensional image of the block 40 in a similar manner to that described with respect to that for the block 20.

The processor 18 produces a three-dimensional image of the block 40 and the three dimensional image of the block 40 comprises a first shade, or colour, corresponding to the material 42, a second shade, or colour, corresponding to a first powder particles 46 and a third shade, or colour, corresponding to the second powder particle 48. The processor 18 analyses the three-dimensional image of the block 40 and counts the number of regions exhibiting the second shade, or colour, and hence counts the corresponding number of first powder particles 46 in the block 40. The processor 18 analyses the three-dimensional image of the block 40 and counts the number of regions exhibiting the third shade, or colour, and hence counts the corresponding number of second powder particles 48. The first and second powder particles 46 and 48 consist of different materials and the different powder particles 46 and 48 affect the intensity of the X-rays received by the X-ray detector 16. The processor 18 then determines the amount of second particles 48 in the powder 44 by determining the fraction of second powder particles 48 by dividing the number of second powder particles 48 counted by the sum of the number of first powder particles 46 counted and the number of second powder particles 48 counted.

The powder 44 may comprise a metal powder, an alloy powder, a ceramic powder, a mixture of a metal powder and an alloy powder, a mixture of a metal powder and a ceramic powder or a mixture of an alloy powder and a ceramic powder.

The molten material 42 may alternatively comprise a polymer/plastic or water and the molten material 42 is solidified after the sample of powder 44 has been added to the molten material 42.

It may be possible to use other types of computed tomography, in place of X-ray computed tomography.

In a third method of determining the proportions of different powders in a powder according to the present invention a sample of a powder is obtained, the powder comprising three different powder particles. This method is substantially the same as that described with reference to the methods described previously. However, this method differs in that the three-dimensional image of the block produced by the processor 18 comprises a first shade, or colour, corresponding to the material, a second shade, or colour, corresponding to a first powder particle, a third shade, or colour, corresponding to a second powder particle and a fourth shade, or colour, corresponding to a third powder particle. The processor 18 analyses the three-dimensional image of the block to count the number of regions exhibiting the second shade, or colour, and hence counts the corresponding number of first powder particles in the block. The processor 18 analyses the three-dimensional image of the block to count the number of regions exhibiting the third shade, or colour, and hence counts the corresponding number of second powder particles. The processor 18 analyses the three-dimensional image of the block to count the number of regions exhibiting the fourth shade, or colour, and hence counts the corresponding number of third powder particles. Finally the processor 18 determines the amount of second particles in the powder by determining the fraction of second powder particles by dividing the number of second powder particles counted by the sum of the number of first powder particles counted, the number of second powder particles counted and the number of third powder particles counted in step.

The powder may comprise a metal powder, an alloy powder, a ceramic powder, a mixture of a metal powder and an alloy powder, a mixture of a metal powder and a ceramic powder or a mixture of an alloy powder and a ceramic powder.

The molten material may alternatively comprise a polymer/plastic or water and the molten material is solidified after the sample of powder has been added to the molten material.

It may be possible to use other types of computed tomography, in place of X-ray computed tomography.

The present invention may be used to determine the proportions of both of the powders in a powder containing two different powder particles, to determine the proportions of one or more of the powders in a powder containing two or more different powder particles or to determine the proportions of all of the powders in a powder containing two or more different powder particles.

The present invention may be used to differentiate between two different powder particles and also between solid and porous powder particles of different types of powder particles.

The present invention permits larger sample sizes of powder to be examined because it is automated and because the powder particles are distributed in three-dimensions rather than two-dimensions. These larger sample sizes greatly increase the reliability of the analysis, because many more data points are available and because it is much easier to ensure that a larger sample size is representative of a production batch than a smaller sample size. An advantage of the present invention is that it uses a three-dimensional method for imaging the powder particles, rather than a two-dimensional method for imaging the powder particles. This enables accurate measurement of the diameter of pores within powder particles and accurate statistics to be generated based on a large number of powder particles with minimal involvement by an operator. The use of three-dimensional imaging eliminates the variability and unreliability of measurement from two-dimensional imaging caused by settling of the powder particles in the sample. The present invention makes settling of the powder particles within the sample irrelevant because the entire sample is analysed together. The use of three-dimensional imaging enables accurate statistics for the distribution of sizes of pores within the powder particles to be determined because the computing system is able to measure the pore diameter at any point on the pore, rather than at a single two-dimensional plane. The use of a low melting point alloy, material, block to encapsulate the powder particles for subsequent high resolution computed tomography enables both high throughput volumetric analysis of large homogeneous samples of powder for porosity content and the generation of accurate statistics characterising the size of any pores in the powder particles. These benefits are enabled by the introduction of a third level of contrast, or colour, in the computed tomography image by the encapsulating low melting point alloy, material, which is distinct from both the powder particles and the pores.

The present invention may be used to determine the proportions of different powder particles, e.g. porous powder particles and solid powder particles, for quality control purposes. The present invention may be used to determine the proportions of different metal powder particles, e.g. porous metal powder particles and solid metal powder particles, for quality control purposes for metal powder particles hot isostatically pressed, for metal powder particles hot isostatically pressed to net shape or near net shape or for metal powder particles used to manufacture or repair components for gas turbine engines.

The present invention may be used to determine the proportions of different powder particles, e.g. powder debris particles in oil systems of engines, e.g. gas turbine engine, internal combustion engines, diesel engines etc and may be used to indicate engine damage and/or which engine component, or components, the powder debris particles had come from.

The invention claimed is:

1. A method of determining the proportions of different powders in a powder comprising the steps of:
   a) obtaining a sample of a powder, the powder comprising powder particles,
   b) preparing a predetermined volume of molten material,
   c) adding the sample of the powder to the molten material,
   d) mixing the sample of the powder into the molten material,
   e) solidifying the mixture of powder and molten material to form a block, the block consisting of the material containing the powder particles,
   f) carrying out computed tomography on the block to produce a three-dimensional image of the block, the three-dimensional image of the block comprising a first shade, or colour, corresponding to the material, a second shade, or colour, corresponding to a first powder particle and a third shade, or colour, corresponding to a second powder particle,
   g) analysing the three-dimensional image of the block to count the number of regions exhibiting the second shade, or colour, and hence count the corresponding number of first powder particles in the block, analysing the three-dimensional image of the block to count the number of regions exhibiting the third shade, or colour, and hence count the corresponding number of second powder particles, and
   h) determining the amount of second particles in the powder by determining the fraction of second powder particles by dividing the number of second powder particles counted in step g) by the sum of the number of first powder particles counted in step g) and the number of second powder particles counted in step g).

2. A method as claimed in claim 1 wherein step a) comprises obtaining a sample of a metal powder, an alloy powder or a ceramic powder.

3. A method as claimed in claim 1 wherein step b) comprises preparing a predetermined volume of a low melting point eutectic alloy.

4. A method as claimed in claim 3 wherein the low melting point eutectic alloy consists of a bismuth-tin eutectic alloy.

5. A method as claimed in claim 1 wherein step b) comprises preparing a predetermined volume of a material selected from the group consisting of a polymer, a plastic and water.

6. A method as claimed in claim 1 wherein the first and second powder particles consist of different materials.

7. A method as claimed in claim 1 wherein the first powder particles are pore free and the second powder particles have pores and the first and second powder particles consist of the same material.

8. A method as claimed in claim 7 further comprising measuring the diameter of each pore in a powder particle.

9. A method as claimed in claim 8 further comprising calculating the mean diameter of the pores, the maximum diameter of the pores, the minimum diameter of the pores or the variance in the diameter of the pores.

10. A method as claimed in claim 1 wherein step f) comprises X-ray computed tomography.

11. A method as claimed in claim 1 wherein step f) comprises carrying out computed tomography on the block to produce a three-dimensional image of the block, the three-dimensional image of the block comprising a first shade, or colour, corresponding to the material, a second shade, or colour, corresponding to a first powder particle, a third shade, or colour, corresponding to a second powder particle and a fourth shade, or colour, corresponding to a third powder particle,
  g) analysing the three-dimensional image of the block to count the number of regions exhibiting the second shade, or colour, and hence count the corresponding number of first powder particles in the block, analysing the three-dimensional image of the block to count the number of regions exhibiting the third shade, or colour, and hence count the corresponding number of second powder particles, analysing the three-dimensional image of the block to count the number of regions exhibiting the fourth shade, or colour, and hence count the corresponding number of third powder particles,
  h) determining the amount of second particles in the powder by determining the fraction of second powder particles by dividing the number of second powder particles counted in step g) by the sum of the number of first powder particles counted in step g), the number of second powder particles counted in step g) and the number of third powder particles counted in step g).

12. A method as claimed in claim 3 wherein step e) comprises freezing the molten material.

13. An apparatus for determining the proportions of different powders in a powder comprising a computed tomography device operable to produce a three-dimensional image of a block, the block consisting of a material containing powder particles, the three-dimensional image of the block comprising a first shade, or colour, corresponding to the material, a second shade, or colour, corresponding to a first powder particle and a third shade, or colour, corresponding to a second powder particle, a processor arranged to analyse the three-dimensional image of the block to count the number of regions exhibiting the second shade, or colour, and hence count the corresponding number of first powder particles in the block, a processor arranged to analyse the three-dimensional image of the block to count the number of regions exhibiting the third shade, or colour, and hence count the corresponding number of second powder particles, and a processor arranged to determine the amount of second particles in the powder by determining the fraction of second powder particles by dividing the number of second powder particles counted by the sum of the number of first powder particles counted and the number of second powder particles counted.

14. An apparatus as claimed in claim 13 wherein the second powder particles comprise pores, the apparatus further comprising a calculator to calculate the mean diameter of the pores, the maximum diameter of the pores, the minimum diameter of the pores or the variance in the diameter of the pores.

15. An apparatus as claimed in claim 13 wherein the computed tomography device comprises an X-ray computed tomography device.

16. A method of determining the proportion of porosity in a powder comprising the steps of:
  a) obtaining a sample of a powder, the powder comprising powder particles,
  b) preparing a predetermined volume of molten material,
  c) adding the sample of the powder to the molten material,
  d) mixing the sample of the powder into the molten material,
  e) solidifying the mixture of powder and molten material to form a block, the block consisting of the material containing the powder particles,
  f) carrying out computed tomography on the block to produce a three-dimensional image of the block, the three-dimensional image of the block comprising a first shade, or colour, corresponding to the material, a second shade, or colour, corresponding to a powder particle and a third shade, or colour, corresponding to a pore in a powder particle,
  g) analysing the three-dimensional image of the block to count the number of regions exhibiting the second shade, or colour, and hence count the corresponding number of powder particles in the block, analysing the three-dimensional image of the block to count the number of regions exhibiting the third shade, or colour, and hence count the corresponding number of powder particles containing a pore, and
  h) determining the amount of porosity in the powder by determining the fraction of powder particles containing pores by dividing the number of powder particles containing a pore counted in step g) by the number of powder particles counted in step g).

17. A method as claimed in claim 16 wherein step a) comprises obtaining a sample of a metal powder, an alloy powder or a ceramic powder.

18. A method as claimed in claim 16 wherein step b) comprises preparing a predetermined volume of a low melting point eutectic alloy.

19. A method as claimed in claim 18 wherein the low melting point eutectic alloy consists of a bismuth-tin eutectic alloy.

20. A method as claimed in claim 16 wherein step b) comprises preparing a predetermined volume of a material selected from the group consisting of a polymer, a plastic and water.

21. A method as claimed in claim 16 further comprising measuring the diameter of each pore in a powder particle.

22. A method as claimed in claim 21 further comprising calculating the mean diameter of the pores, the maximum diameter of the pores, the minimum diameter of the pores or the variance in the diameter of the pores.

23. A method as claimed in claim 16 wherein step f) comprises X-ray computed tomography.

24. A method as claimed in claim 16 wherein step e) comprises freezing the molten material.

* * * * *